United States Patent [19]
Muller et al.

[11] 4,072,660
[45] Feb. 7, 1978

[54] PROCESS FOR THE MANUFACTURE OF RESORCINOLS

[75] Inventors: Werner Heinrich Müller, Aldersbach; Hansjörg Hey, Hofheim, Taunus, both of Germany; Tomas Weil, Sao Paulo, Brazil

[73] Assignee: Hoechst Aktiengesellschaft, Frankfurt am Main, Germany

[21] Appl. No.: 709,291

[22] Filed: July 28, 1976

[30] Foreign Application Priority Data

July 30, 1975 Germany .............................. 2533920

[51] Int. Cl.$^2$ ...................... C07C 39/08; C07C 39/06; C07C 43/22
[52] U.S. Cl. ............................... 260/621 H; 260/625; 260/613 B; 260/465 F
[58] Field of Search ............... 260/625, 621 R, 621 H, 260/595, 613 D, 621 D, 613 B, 465 F

[56] References Cited

U.S. PATENT DOCUMENTS

| | | | |
|---|---|---|---|
| 1,926,632 | 9/1933 | Roka | 260/595 |
| 3,627,833 | 12/1971 | Tobices | 260/621 H |
| 3,691,102 | 9/1972 | Swift | 260/625 |
| 3,900,522 | 8/1975 | Greco | 260/621 H |
| 3,932,511 | 1/1976 | Schaafsma | 260/625 |

*Primary Examiner*—James O. Thomas, Jr.
*Assistant Examiner*—W. B. Lone
*Attorney, Agent, or Firm*—Curtis, Morris & Safford

[57] ABSTRACT

Resorcinols are prepared by reacting 4-oxocarboxylic acid esters or δ-enollactones with a strong base in a glycol dialkyl ether as solvent and by subsequent dehydrogenating the acidified reaction product.

8 Claims, No Drawings

PROCESS FOR THE MANUFACTURE OF RESORCINOLS

This invention relates to a process for the manufacture of resorcinols.

It is known to produce cyclohexanediones-1,3 by cyclization of 4-oxocarboxylic acid esters or by isomerization of δ-enollactones of the corresponding 4-oxocarboxylic acids with strong bases in certain solvents, for example, carboxylic acid amides, sulfoxides, sulfones, or phosphoric acid amides.

Cyclohexanediones can be transformed by dehydrogenation into resorcinols which are used as components for making artificial resins, in rubber industries and wood glue industry, as coupling component in making diazotypes, or as antiseptic. For this aromatization of the cyclohexanediones the catalytic dehydrogenation in polyglycol ethers as solvent gives especially good results.

The important disadvantage of the manufacture of resorcinols by this two-stage process is the necessary isolation of the cyclohexanediones from the reaction products since the known solvents which are especially suitable for the cyclization, such as carboxylic acid amides, phosphoric acid amides, sulfones and sulfoxides, give poor resorcinol yields in the subsequent dehydrogenation.

It has now been found that the resorcinols can be prepared from the specified compounds without isolation of the intermediarily formed cyclohexandiones.

The present invention provides a process for the manufacture of resorcinols of the formula

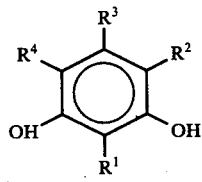

in which the radicals $R^1$ to $R^4$, which may be identical or different, represent hydrogen, alkyl groups having up to 12 carbon atoms, $R^1$ and $R^2$ can additionally represent alkoxy groups having up to 4 carbon atoms or aryl groups having up to 10 carbon atoms, and $R^3$ can additionally represent a cyano group or a carbalkoxy group having up to 6 carbon atoms, which comprises reacting 4-oxocarboxylic acid esters of the formula

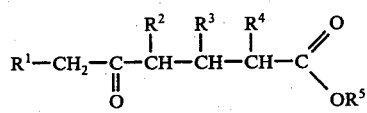

in which the radicals $R^1$ to $R^4$ have the aforesaid meaning and $R^5$ is an alkyl radical having up to 6 carbon atoms, or δ-enollactones of the formula

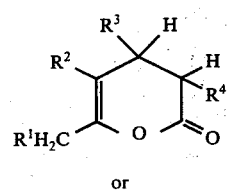

or

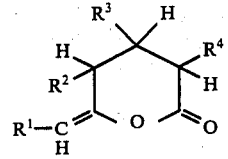

in which $R^1$ to $R^4$ have the aforesaid meaning, with a strong base in an ether or a mixture of several ethers of the formula $$R^6 + \left[ O - \underset{\underset{R^7}{|}}{CH} - \underset{\underset{R^8}{|}}{CH} \right]_n OR^9$$

in which $n$ is in the range of from 1 to 5 and $R^6$ to $R^9$, which may be identical or different, represent alkyl groups having up to 12 carbon atoms and, with the exception of $R^6$ and $R^9$, can represent also hydrogen, as solvent, acidifying the reaction product and dehydrogenating it under a pressure of from 0.1 to 20 atmospheres and at a temperature of 150° to 350° C in the presence of a catalyst containing a noble metal of subgroup 8 of the Periodic Table.

The two isomeric lactones of formulae III and IV should be considered inner esters of 4-oxocarboxylic acid, whilst the compound of formula II is a regular ester of the said acid.

Suitable alkyl groups for substituents $R^1$ to $R^9$ are straight chain, branched or cyclic radicals having up to 12 carbon atoms, preferably up to 6 carbon atoms, for example methyl, ethyl, propyl, butyl, pentyl, hexyl, octyl, decyl, dodecyl, cyclopentyl or cyclohexyl. Alkyl groups containing a double bond are also suitable, for example the allyl group.

The alkyl groups can also carry substituents, for example the phenyl group, keto group, carbamide group, or nitrile group, or an alkoxy group or a carbalkoxy group having up to 6 carbon atoms, for example methoxy, ($-OCH_3$), ethoxy ($-OC_2H_5$), carboxymethyl ($-COOCH_3$) or carboxy ethyl ($-COOC_2H_5$).

Suitable aryl groups for the substituents $R^1$ and $R^2$ are the phenyl and the naphthyl group. The aryl groups may also be substituted, for example by halogen atoms, especially fluorine and chlorine, alkyl groups having up to 6 carbon atoms, or by trifluoromethyl-, pentafluoroethyl or nitro groups, other suitable substituents are alkoxy groups having up to 6 carbon atoms, for example the methoxy or ethoxy group.

As strong bases there can be used the alkali metal or alkaline earth metal alcoholates, oxides, amides and hydrides or the metals per se.

Especially favorable solvents are the di-, tri-, tetra-, and penta-ethylene glycol-($C_1$-$C_6$) dialkyl ethers or mixtures thereof, in the first place the following compounds: monoethylene glycol dimethyl ether, diethylene glycol dimethyl ether, diethylene glycol diethyl ether, triethylene glycol diethyl ether, tetraethylene glycol diethyl ether, triethylene glycol dimethyl ether, tetraethylene glycol dimethyl ether, pentaethylene glycol dimethyl ether, methyl glycol tert.butyl ether, ethyl glycol tert. butyl ether, butyl glycol tert.butyl ether, methyl diglycol tert. butyl ether, ethyl diglycol tert.butyl ether, butyl diglycol tert. butyl ether.

The specified ethers can be diluted with other solvents, for example with methanol, ethanol, isopropanol, ethylene glycol, n-butanol, diethyl ether, diisopropyl ether, ethylene glycol monoethyl ether, tetrahydrofurane, dioxane, xylene, acetonitrile, ethyl acetate, propanediol diacetate.

In general, the 4-oxocarboxylic acid ester or the δ-enollactones are reacted with the strong base in the aforesaid ethers at a temperature of from 0° to 150° C, preferably 15° to 90° C at atmospheric pressure, either continuously or discontinuously. The ethers used as solvent are generally used in a proportion by weight of from 20:1 to 1:1, calculated on the 4-oxyocarboxylic acid or the δ-enollactone. The salt of the respective cyclohexanedione formed in the reaction is transformed into the cyclohexanedione by acidification and the dione is then dehydrogenated.

The total reaction can be illustrated by the following scheme using the 5-oxohexanoic acid methyl ester or 6-methyl-3,4-dihydro-2-pyranone, i.e. the unsaturated lactone of 5-oxohexanoic acid:

to carrier materials, for example carbon, aluminium oxide, silicic acid, alumosilicates, magnesium silicates, magnesium oxide, calcium oxide, titanium dioxide, and asbestos. Especially good results are obtained with palladium supported on carbon. The concentration of the noble metal is preferably in the range of from 0.02 to 20%, calculated on the weight of the carrier material, preferably 0.1 to 10% by weight.

The dehydrogenation can be carried out either continuously or discontinuously at a temperature in the range of from 150° to 350° C, preferably 180° to 260° C since at the latter temperatures the selectivity is especially high with a very rapid performance of the dehydrogenation. The reaction is preferably carried out in the liquid phase, but it may also be carried out in the gaseous phase.

The reaction pressure during the course of dehydrogenation is in the range of from 0.1 to 20 atmospheres, it is preferably chosen in a range that it is sufficient to maintain a liquid phase.

It proved advantageous to maintain at a low level the

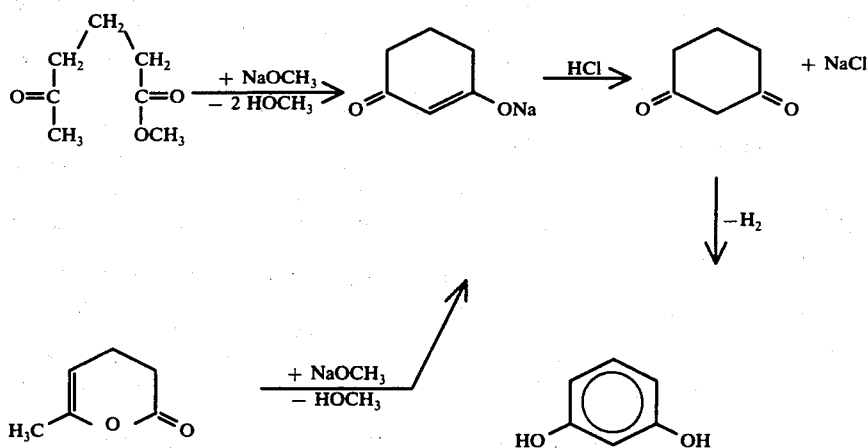

Suitable starting compounds are, for example, the $C_1$ to $C_6$ alkyl esters or the unsaturated lactones of the following acids: 5-oxohexanoic acid, 5-oxoheptanoic acid, 5-oxooctanoic acid, 5-oxononanoic acid, 2-methyl-5-oxohexanoic acid, 4-methyl-5-oxohexanoic acid, 2,4-dimethyl-5-oxohexanoic acid, 3-methyl-5-oxohexanoic acid, 3,4-dimethyl-5-oxyhexanoic acid, 3-phenyl-5-oxohexanoic acid, 4-phenyl-5-oxohexanoic acid, 6-phenyl-5-oxohexanoic acid, 3-cyano-5-oxohexanoic acid, 3-carbomethoxy-5-oxohexanoic acid, 4-methyl-5-oxoheptanoic acid, 4-methyl-5-oxooctanoic acid, 4-ethyl-5-oxohexanoic acid, 4-propyl-5-oxohexanoic acid, 4-isopropyl-5-oxohexanoic acid, 4-butyl-5-oxohexanoic acid, 4-pentyl-5-oxohexanoic acid, 4-hexyl-5-oxohexanoic acid, 4- -methoxy-5-oxohexanoic acid, 4-acetylheptanoic-1,7 diacid and 5-oxononanoic-1,7 diacid.

To prepare the cylcohexanediones the following method proved to be especially advantageous: the 4-oxocarboxylic acid ester or the δ-enollactone is added, while intensely stirring, to a mixture of the strong base with the solvent (ether). As soon as an amount of ester or lactone equivalent to the strong base is added, the reaction mixture is acidified with hydrochloric acid to pH 3 to 4, the sodium hydrochloride formed is separated and the cyclohexanedione solution is directly dehydrogenated.

Suitable noble metals for the dehydrogenation catalysts are, in the first place, palladium, platinum, ruthenium and rhodium. In general, the catalysts are applied partial pressure of the hydrogen formed in the dehydrogenation so that the equilibrium is shifted in favor of the dehydrogenation and a hydrogenation or hydrogenolysis of the starting compounds and the final products is avoided. This low partial pressure of hydrogen can be ensured by flushing the reaction system with an inert gas, for example nitrogen or carbon dioxide.

Especially suitable solvents are the aforesaid di-, tri-, tetra-, and penta-ethylene glycol ($C_1$-$C_6$) dialkyl ethers since they boil at atmospheric pressure in the preferred temperature range of from 180° to 260° C, which fact is very favorable for the process as it can be carried out without pressure application and in the preferred temperature range the dehydrogenation takes place especially rapidly and with high selectivity under reflux conditions. The efficiency of the dehydrogenation is increased by intense stirring of the reaction mixture during its contact with the catalyst.

The generated hydrogen additionally provides for thorough stirring of the reaction mixture. When the reaction is terminated, the catalyst is separated from the reaction mixture by filtration and the resorcinol is obtained in the pure state by distillation of the filtrate.

The following mode of operation proved to be particularly advantageous with continuous dehydrogenation: the cyclohexanedione solution is transferred, via a preheater, into a dehydrogenation mixture consisting of solvent and dehydrogenation catalyst while simultaneously a corresponding amount of the reaction mixture containing the formed resorcinol is discharged. The catalyst is retained in the reactor by a frit, or it is separated, for example by means of a hydrocyclone, and returned into the reactor. After having been separated from the resorcinol by distillation, the solvent is recycled into the first stage of the process, i.e. the reaction of 4-oxocarboxylic acid ester or δ-enollactone.

The dehydrogenation can be carried out with a fixed bed catalyst or with a catalyst suspended in the reaction solution by vigorous stirring.

When the process is carried out with a catalyst supported on a carrier material its particle size is generally in the range of from 0.01 to 5 mm, preferably 0.05 to 1 mm. Smaller particles have the disadvantage of being difficult to separate from the reaction solution while larger particles are difficult to maintain in suspension and have a low dehydrogenation speed. In general, the suspension contains 0.1 to 40 parts by weight of supported catalyst for 100 parts by weight of solution. The preferred ratio is 1 to 30 parts by weight of supported catalyst for 100 parts by weight of solution.

The following examples illustrate the invention.

EXAMPLE 1

A 1 liter four-necked flask, provided with mechanical stirrer, dropping funnel, thermometer and reflux condenser was charged with a mixture of 30 grams of sodium methylate and 400 grams of diethylene glycol diethyl ether. During the course of 1 hour at 25° C 48 grams of 5-oxohexanoic acid methyl ester were uniformly added. When the ester addition was terminated, gas chromatographic analysis indicated that the ester had completely reacted. Next, the reaction mixture was acidified to pH 3.5 by adding 46 ml of concentrated hydrochloric acid and the formed crystalline sodium chloride was filtered off with suction. Gas chromatographic analysis of the filtrate indicated a yield of cyclohexanedione-1,3 of 35.0 grams ≈ 94%. 75 g of the filtrate which, according to gas chromatographic analysis, contained 6 grams of cyclohexane-dione-1,3 were added, over a period of 1 hour, to a dehydrogenation mixture heated to 185°–190° C and consisting of 50 ml diethylene glycol diethyl ether and 1 gram of catalyst (0.1 gram palladium on 0.9 gram of carbon). As soon as the development of gas was terminated (1210 ml), the reaction mixture was cooled while flushing with nitrogen, the catalyst was filtered off with suction, washed with a little diethylene glycol diethyl ether, the filtrate was analyzed by gas chromatography and then distilled under reduced pressure. After a solvent fraction (boiling point under 15 mm Hg 78–84° C) and a small amount of phenol, pure resorcinol was obtained.

Yield:
resorcinol 5.2 g ≏ 88 mol %
phenol 0.13 g ≏ 2.6 mol %.

EXAMPLE 2

In a 1 liter four-necked flask equipped with dropping funnel, reflux condenser and mechanical stirrer a mixture of 300 ml of triethylene glycol dimethyl ether and 30 grams of NaOCH$_3$ was heated to 70° C and, over a period of 30 minutes, 37.5 grams of 6-methyl-3,4-dihydro-2-pyranone were continuously added. The subsequent gas chromatographic analysis showed a complete reaction of the enollactone. The reaction mixture was acidified with 44.6 ml of concentrated hydrochloric acid to a pH of 3 and the precipitated sodium chloride was filtered off with suction. Gas chromatographic analysis of the filtrate indicated 31.5 grams ≈ 85% of cyclohexanedione-1,3. 66 Grams of the filtrate containing 6.0 grams of cyclohexanedione-1,3 were added dropwise, over a period of 1 hour, to a dehydrogenation mixture of 60 ml of triethylene glycol dimethyl ether and 1.0 gram of catalyst (0.1 g palladium on 0.9 g of carbon carrier) heated to 210°–212° C and the course of the dehydrogenation was followed by the gas development. When the reaction was terminated the reactor was flushed with nitrogen, the catalyst was filtered off and the filtrate was analyzed by gas chromatography.

Yield:
resorcinol 5.1 g = 86.4%
phenol 0.2 g = 4%.

EXAMPLE 3

The apparatus as used in Examples 1 and 2 was charged with a mixture of 350 ml of diethylene glycol diethyl ether and 25 grams of sodium methylate. Then 53 grams of an isomer mixture (78 : 22) of 4-methyl-5-oxohexanoic acid methyl ester and 5-oxoheptanoic acid methyl ester (boiling point 101°–103° C under 12 mm Hg) were added at 30° C over a period of 70 minutes. Subsequent gas chromatographic analysis indicated complete conversion. The reaction mixture was acidified with 37 ml of concentrated hydrochloric acid, the sodium chloride was filtered off and the filtrate was analyzed.

Yield:
29 grams = 68.7% of 4-methyl-cyclohexandione-1,3,
8.1 grams ≏ 19.2% of 2-methyl-cyclohexanedione-1,3.

20% of the filtrate containing 7.4 grams of a mixture of 4-methylcyclohexanedione-1,3 and 2-methyl-cyclohexanedione-1,3 (78/22) were added, over a period of 1 hour, to a dehydrogenation mixture, preheated to 190° C, of 60 ml of diethylene glycol diethyl ether and 1 gram of catalyst (0.1 g palladium on 0.9 g of carbon). When the development of gas was terminated the catalyst was filtered off and the filtrate was analyzed by gas chromatography.

Yield:
4-methyl-resorcinol 4.94 grams ≏ 68 %
2-methyl-resorcinol 1.3 grams ≏ 18 %.

EXAMPLE 4

In the same apparatus as used in the preceding examples 57 grams of 4-methyl-5-oxoheptanoic acid methyl ester (boiling point 106° C under 12 mm Hg) were added, over a period of 70 minutes at 70° – 80° C, to a mixture of 25 grams of NaOCH$_3$ in 350 ml of diethylene glycol diethyl ether. Subsequent gas chromatographic analysis indicated complete conversion. After acidification with 37.5 ml concentrated hydrochloric acid, the sodium chloride was filtered off and the filtrate was analyzed.

Yield: 44.0 grams ≏ 95 % off 2,4-dimethyl-cyclohexanedione-1,3.

The subsequent dehydrogenation of one half of the above filtrate in the presence of a palladium/carbon catalyst at a temperature of 184° – 185° C during the course of 2 hours yielded 2.25 of off-gas. After separation of the catalyst first the diethylene glycol ether was distilled off and then the formed 2,4-dimethyl-resorcinol.

Yield: 18.8 grams ≙ 85 % (melting point 107° C recrystallized from benzene) crystallizing in the receiver.

EXAMPLE 5

In the same apparatus as used in the preceding example 62.7 grams of a mixture of 4-isopropyl-5-oxohexanoic acid isopropyl ester and 7-methyl-5-oxo-octanoic acid isopropyl ester (80/20) were added, over a period of 60 minutes at 30° C, to a mixture of 25 grams of sodium methylate in 300 ml of diethylene glycol diethyl ester. After acidification with 37 ml of concentrated hydrochloric acid and separation by filtration of the sodium chloride, gas chromatographic analysis of the filtrate indicated a yield of 38.1 grams ≙ 74.2 % of 4-isopropyl-cyclohexanedione-1,3 and 9.2 grams ≙ 18 % of 2-isopropyl-cyclohexanedione-1,3.

The filtrate was divided into two aliquots from one of which pure 4-isopropyl-cyclohexanedione-1,3 (melting point 105° C) and 2-isopropyl-cyclohexanedione-1,3 melting point 135° - 139° C, acid number 387 ≙ molecular weight 155) was obtained after distillation of the solvent by repeatedly crystallizing the residue from ethyl acetate/diethyl ether. The other portion was added at 192° C over a period of 2 hours to a dehydrogenation mixture consisting of 80 ml of diethylene glycol diethyl ether and 2 grams of dehydrogenation catalyst (0.2 g palladium on 1.8 g of carbon carrier). When the development of gas was terminated, the catalyst was filtered off and the filtrate was analyzed by gas chromatography.

Yield:
4-isopropyl-resorcinol 17.1 grams ≙ 73.3 %
2-isopropyl-resorcinol 4.1 grams ≙ 17.6 %.

After distillation of the solvent a fraction was obtained at 160° C under 3 mm Hg from which, after crystallization from chloroform, pure isopropyl-resorcinol melting at 98° - 99° C was obtained in the form of colorless crystals. Besides a small amount of 4-isopropyl-resorcinol, the mother liquor contained the formed 2-isopropyl-resorcinol.

EXAMPLE 6

In the same apparatus as used in the preceding examples 75 grams of 4-n-hexyl-5-oxohexanoic acid methyl ester were added, over a period of 1 hour at 27° - 30° C, to a mixture of 25 grams of sodium methylate and 350 ml of diethylene glycol diethyl ether and the reaction mixture was acidified to pH 4 with concentrated hydrochloric acid. After separation of the sodium chloride, the filtrate was analyzed by gas chromatography.

Yield: 59.4 grams ≙ 91 % of 4-n-hexylcyclohexanedione-1,3.

The filtrate was divided into two aliquots. From the first portion the solvent was distilled off and pure 4-n-hexyl-cyclohexanedione (melting point 61° - 63° C, acid number 290 ≙ molecular weight 196.6, theory 196) was obtained by crystallization from ethyl acetate. The other portion was dehydrogenated using a palladium/carbon catalyst (0.2 g palladium on 1.8 grams of carbon carrier) under the aforesaid conditions whereby 25.9 grams( ≙ 88 % yield) of 4-n-hexyl-resorcinol were obtained.

EXAMPLE 7

A 500 ml four-necked flask provided with thermometer, reflux condenser, mechanical stirrer and dropping funnel was charged with 250 ml diethylene glycol diethyl ether and 25 grams of NaOCH₃. Then a mixture of 30 ml diethylene glycol diethyl ether and 20 grams of 4-methoxy-5-oxohexanoic acid methyl ester was continually added over a period of 60 minutes at 27° - 31° C. The 4-methoxy-5-oxohexanoic acid methyl ester had been prepared analogous to the 5-oxohexanoic acid methyl ester (German Offenlegungsschrift No. 2,325,160) from methoxyacetone and methyl acrylate. Boiling point 87° C under 4 mm Hg, NMR spectrum in CDCl₃, TMS as internal standard:

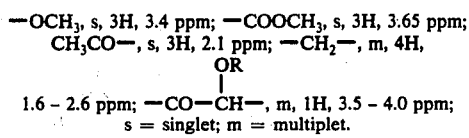

—OCH₃, s, 3H, 3.4 ppm; —COOCH₃, s, 3H, 3.65 ppm;
CH₃CO—, s, 3H, 2.1 ppm; —CH₂—, m, 4H,
OR
|
1.6 – 2.6 ppm; —CO—CH—, m, 1H, 3.5 – 4.0 ppm;
s = singlet; m = multiplet.

The subsequent gas chromatographic analysis indicated a complete conversion of the ester. The reaction mixture was then acidified with 42 ml of concentrated hydrochloric acid and the formed sodium chloride was filtered off with suction.

81 grams of the filtrate (305 grams total weight) were added dropwise over a period of 80 minutes to a dehydrogenation mixture preheated to 185° - 190° C and consisting of 60 ml of diethylene glycol diethyl ether and 1 gram of palladium/carbon catalyst (0.9 g C, 0.1 g Pd). When the development of gas had ceased the reactor was flushed with nitrogen, the catalyst was filtered off with suction and the filtrate was distilled under reduced pressure. After a glycol ether fraction 4.3 grams of a product distilled over a 136° - 145°C under 2 mm Hg, which according to gas chromatography, thin layer chromatography and nuclear magnetic resonance spectrum, contained 85 % of 4-methyl-resorcinol.

What is claimed is:

1. In a process for the manufacture of resorcinols of the formula

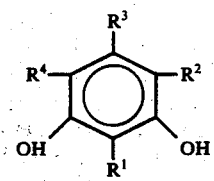

in which the radicals R¹ to R⁴, which may be identical or different, represent hydrogen, alkyl groups having up to 12 carbon atoms, R¹ and R² can additionally represent alkoxy groups having up to 4 carbon atoms or aryl groups having up to 10 carbon atoms and R³ can additionally represent a cyano group or carbalkoxy group having up to 6 carbon atoms, by reacting in a first step 4-oxo-carboxylic acid esters of the formula

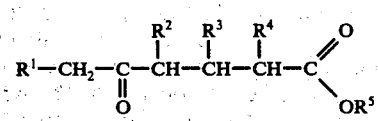

in which the radicals R¹ to R⁴ have the aforesaid meaning and R⁵ is an alkyl radical having up to 6 carbon atoms, or δ-enollactones of the formula

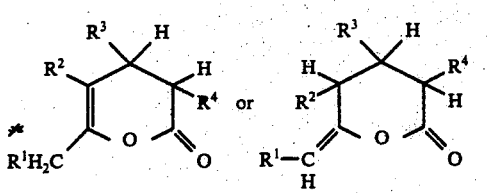

in which $R^1$ to $R^4$ have the aforesaid meaning, with a strong base selected from the alkali and alkaline earth metals and their alcoholates, oxides, amides and hydroxides to form a cyclohexane dione and in a second step dehydrogenating said cyclohexane dione under a pressure of from 0.1 to 20 atmospheres at a temperature of from 150° to 350° C. in the presence of a catalyst containing a noble metal of the 8th subgroup of the Periodic Table to form said resorcinol, the improvement which comprises carrying out both of said steps without intermediate isolation of said cyclohexane dione in a solvent solution of a solvent which is an ether or a mixture of several ethers of the formula $$R^6 \left[ -O-\underset{|}{\overset{R^7}{C}}H-\underset{|}{\overset{R^8}{C}}H- \right]_n OR^9$$

in which $n$ is in the range of from 1 to 5 and $R^6$ to $R^9$, which may be identical or different, represent alkyl groups having 1 to 12 carbon atoms and, with the exception of $R^6$ and $R^9$, may also represent hydrogen.

2. The process of claim 1, wherein the strong base is an alkali metal or an alcoholate, oxide, amide, or hydride of an alkali metal.

3. The process of claim 1, wherein the strong base is an alkaline earth metal or an alcoholate, oxide, amide or hydride of an alkaline earth metal.

4. The process of claim 1, wherein the 4-oxo-carboxylic acid ester or the δ-enollactone is reacted with the strong base at a temperature of from 0° to 150° C.

5. The process of claim 1, wherein the solvent for the reaction of the 4-oxo-carboxylic acid or the δ-enollactone with the strong base is a di-, tri-, tetra-, or pentaethylene glycol ($C_1$-$C_6$) dialkyl ether.

6. The process of claim 1, wherein the noble metal of the catalyst is palladium.

7. The process of claim 6, wherein the palladium is supported on a carbon carrier.

8. The process of claim 1, wherein the dehydrogenation is carried out at a temperature of from 180° to 260° C.